United States Patent [19]
Eden et al.

[11] Patent Number: 5,366,873
[45] Date of Patent: Nov. 22, 1994

[54] DEVICE AND METHOD FOR USE IN DETECTING MICROORGANISMS IN A SAMPLE

[76] Inventors: Gideon Eden; Ruth Eden, both of 2210 Brockman Blvd., Ann Arbor, Mich. 48104

[21] Appl. No.: 892,581

[22] Filed: Jun. 3, 1992

[51] Int. Cl.⁵ .......................... C12Q 1/04; C12M 1/34
[52] U.S. Cl. .................................. 435/34; 435/291; 435/296; 435/299; 435/808; 435/311
[58] Field of Search ................. 435/4, 8, 29, 30, 31, 435/32, 33, 34, 39, 40, 291, 296–301, 310, 311, 808, 810; 422/55, 58, 59, 68.1, 82.05, 82.06, 82.07, 82.08, 82.09, 82.11, 101, 102; 436/164, 165, 169, 172, 177, 174, 178, 805, 807, 810; 356/51, 436–439, 440, 441, 442, 244, 246, 39; 250/343, 573, 576

[56] References Cited
U.S. PATENT DOCUMENTS

| | | | |
|---|---|---|---|
| 2,992,974 | 7/1961 | Belcove et al. | 435/296 |
| 3,756,920 | 9/1973 | Kelbaugh et al. | 435/808 |
| 3,990,849 | 11/1976 | Lee et al. | 436/177 |
| 4,945,060 | 7/1990 | Turner et al. | 435/291 |
| 5,155,019 | 10/1992 | Sussman et al. | 435/808 |

FOREIGN PATENT DOCUMENTS

| | | | |
|---|---|---|---|
| 0104001 | 3/1984 | European Pat. Off. | 435/296 |
| 0448923 | 10/1991 | European Pat. Off. | 435/291 |

*Primary Examiner*—Michael G. Wityshyn
*Assistant Examiner*—William H. Beisner
*Attorney, Agent, or Firm*—Basile and Hanlon

[57] ABSTRACT

A new device and method to detect the presence of live microorganisms are described. The device employs a liquid phase which supports microbial growth by utilizing appropriate media. A secondary phase which consists of semi-liquid material forms a barrier layer through which only small particles can diffuse and which prevent the presence of any large particles. Noise-free optical measurements are carried out at the barrier layer which are indicative of metabolic changes associated with microbial growth.

14 Claims, 2 Drawing Sheets

DEVICE AND METHOD FOR USE IN DETECTING MICROORGANISMS IN A SAMPLE

TECHNICAL FIELD

The present invention relates to devices for detecting microbial growth from a sample substance and, more particularly, relates to means for detecting microbial growth from a sample.

BACKGROUND OF THE INVENTION

It is necessary to test various industrial substances, such as, food, pharmaceuticals, cosmetics and water for microbial contamination. One area of biological testing of food, dairy, pharmaceutical, cosmetic and related types of products involves the estimation of total numbers of bacteria, yeasts and molds as well as concentrations of specific groups of organisms within the material. One widely used method is known as the "Standard Plate Count" method and involves culturing a diluted sample of the product in an agar growth medium. The plates containing the sample and the growth medium are incubated (e.g., 32° C.–40° C.) for 24 hours to 5 days depending upon the assay. After incubation, colonies of microorganisms which have grown in the agar are counted.

Colorimetric methods have been successfully used to classify microorganisms in clinical samples (e.g., PASCO by Difco, Detroit, Mich.). Although it would be desirable to utilize a colorimetric method, or any other optical method, for detecting microbial growth in industrial samples, the solid substances of the test samples disposed in an aqueous media usually cause optical interference for a detection system. More specifically, when solid substances are disposed in a media to allow for culturing microorganisms, the colorimetric detection system must pass light either through or reflect light from the media containing the solid substance. In most of the cases the solid substances interfere with the spectral characteristics of the media, yielding a poor signal to noise ratio of the detection system.

The present invention provides a solution to the above-discussed problems by providing a detection system which excludes interferences from any substance in the zone of the device through which the measurement is made.

A device for continuously monitoring the biological activity in a specimen is described in U.S. Pat. No. 4,945,060, issued Jul. 31, 1990. The present invention employs a different approach and thereby provides a substantial improvement over this known device in the simplicity of its manufacture and ease of using the device without compromising the integrity of the test results.

SUMMARY OF THE INVENTION

In accordance with the present invention, there is provided a device and method for detecting microbial growth from a sample substance. The device includes a container which is at least partially transparent and fluid disposed in the container for cultivating microorganisms therein. An indicator substance is disposed in the fluid layer for undergoing transformation in the presence of microorganism growth. A second layer, composed of semi-fluid substance, indicators and other substances such as growth media is disposed in the container. The substances within the semi-fluid phase are in equilibrium with the substances in the fluid layer and provide a barrier to solid substances introduced into the fluid layer while providing a zone within which changes in the indicator substance due to microbial growth can be detected.

FIGURES AND THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Generally, the present invention provides a device for detecting microbial growth from a sample substance wherein the device includes a container which is at least partially transparent. A fluid layer is disposed in the container for cultivating microorganisms therein. An indicator substance is disposed in the fluid layer for undergoing transformation in the presence of microorganism growth. A barrier layer is disposed in the container which is a semi-fluid substance, the fluid portion of which is the same composition as the fluid layer in which the microorganisms are cultivated. Therefore the fluid in the semi-fluid layer is in equilibrium with the fluid layer. The semi-fluid substance provides a barrier to solid substances introduced into the fluid layer while providing a zone within which changes in the indicator substance due to microbial growth can be detected.

More specifically, the barrier layer is comprised of gelling agents such as agar. In carrying out the present invention, any type of gelling substance or agar, as defined in the Merck Index, can be utilized. There are several commercial gelling products available which are suitable, including gelatin, carrageenan and pectin.

The important property of such gelling agents used in the present invention is their ability to transfer ions such as H+ and small molecules, while blocking out bacteria and larger debris particles. If the concentration of the small particles change due to organism growth (e.g., pH or Redox reactions) the concentration of the identical particles in the barrier layer will track those changes as well. The diffusion coefficient of the barrier layer determines the rate in which variations in the liquid layer are tracked by identical changes in the barrier layer.

Figure 1:
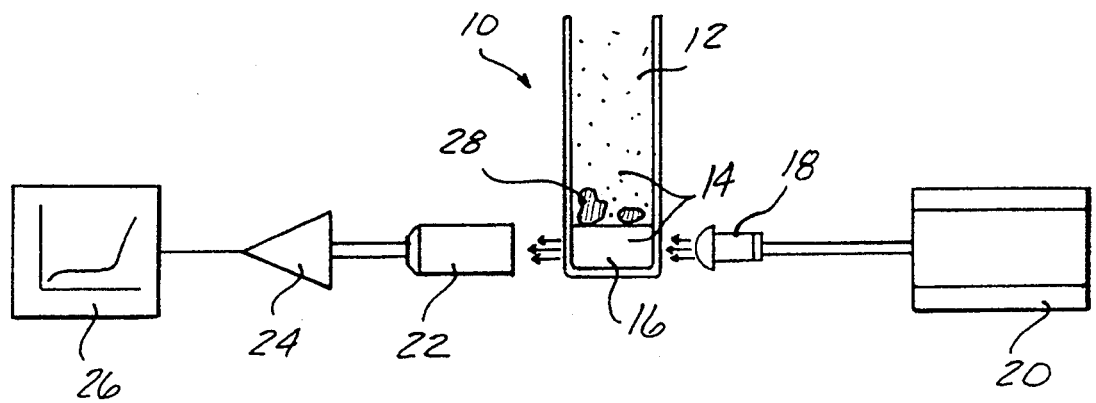
FIG. 1 shows specific components which can be utilized in the present invention.

FIG. 1 illustrates a typical configuration of the various components of a system which can be utilized in accordance with this invention. The vial 10 is made of transparent material (e.g., glass, transparent plastics). The barrier layer 16 may be composed of any available agar (e.g., Muller Hinton Agar by Difco, Detroit, Mich.) and non-toxic dye 14 (e.g., Bromcresol Purple by Sigma, St. Louis, Mo.). This layer is manufactured by dispensing said mixture, thermally sterilized, to the bottom of the vial 10, and letting it solidify at room temperature. A sterile mixture of the liquid media 12 and dye 14 is poured at room temperature on top of the barrier layer.

The tested sample 28 is placed in the fluid layer. The vial 10 is then placed in an incubating device, at an appropriate temperature, to promote growth of organisms. The incubating device can be an air incubator, heating and cooling blocks or heat exchanger.

A light source 18 is positioned at the bottom part of the vial 10 such that the transmitted light is directed through the transparent walls of the vail 10 and the barrier layer 16. The light source can range from various incandescent lamps through gas charged lamps, lasers and light emitting diodes (LED's). In the preferred embodiment of the invention, yellow, orange, green and blue LED's are utilized, depending upon the spectral characteristics of the layer 16. The LED's are controlled by the controller 20 which provides electrical energy which is spatially uniform and stable.

In the preferred embodiment the optical transmissive properties of the layer 16 are time-monitored. However, in the general case any optical changes, such as reflectance or fluorescence, may be measured and analyzed.

The dynamic changes of the transmitted light, which is the indicator of bacterial activity, is converted to electrical energy utilizing a light sensor 22. Although a wide variety of sensors may be utilized, e.g., photo voltaic, photodiodes, phototransistors, photo multipliers, charged coupled devices (CCD) and multi-channel devices low cost solid state sensors can be employed due to the high energy of light reaching the sensor. Therefore each vial can have its own pair of light source and sensor eliminating complex mechanical indexing devices utilized in optical readers, thereby increasing the reliability and the operating life of the instrument.

In the preferred embodiment, readings are taken every six minutes and the analog data is converted by the converter 24 to digital form. The process data is transferred to a processor 26 where it can be displayed, stored and analyzed for real time detection.

The present invention provides an improvement over the devices currently available as represented by that shown in U.S. Pat. No. 4,945,060, the relevant portions of which are incorporated herein by reference, particularly the portions relating to indicator substances, detector means, growth media and continuous monitoring.

The gelling agent or agar is positioned in the container such that it is in a transparent region of the container to facilitate measurement of changes in this phase of the system when in use. If the container is a vial or tube, typically the agar could be placed at the bottom of such receptacle, as illustrated in FIG. 1, and would be approximately 2 to 3 mm thick. The agar also could be in the form of a disc, attached to any wall of the container or other configuration as may be convenient in accomplishing the measurement which is the object of the present invention.

The semi-fluid layer, e.g., the agar or gelling phase is situated in the liquid phase within the container such that the liquid substances within the agar are in equilibrium with the remaining liquid in the container. In the practice of the present invention the liquid phase within the container is a liquid medium suitable for culturing microorganism growth. A sample of a substance which may harbor microorganisms is placed in the liquid phase in the container and incubated to promote growth of the microorganisms. When microorganisms are present, their growth will result in changes in the composition of the liquid phase throughout the container inasmuch as the liquid in the semi-fluid or agar phase is in equilibrium with the remainder of the liquid in the container. The contents of the liquid growth medium can be selected to result in a wide variety of changes in the liquid composition that can be detected and measured as set forth in more detail below. The change in the composition of the liquid growth medium can be detected and measured in the semi-fluid phase which is free of the sample that is being tested and free of microorganisms. The sample being tested is usually too large molecularly to penetrate the agar phase as are the microorganisms. Thus, the semi-fluid phase provides a zone within which changes in the liquid phase, brought on by microorganism growth, can be readily detected and measured without any interference from the test sample.

The liquid phase of the present invention is a medium suitable for the promotion of microorganism growth and for the maintenance of the viability of the microorganisms. Such growth media are well known in the art.

The liquid phase contains one or more indicator substances which are capable of undergoing some type of transformation in the presence of microorganism growth that can be detected and measured. In its simplest form the indicator substance could be a dye that would change in color or intensity in the presence of microorganism growth. Typical dyes useful in the present invention include pH indicators such as Bromcresol Purple, Phenol Red, Bromcresol Green, Bromphenol Blue, Bromthymol Blue; and Redox indicators such as resazurin, methylene Blue, tetrazolium and thionine.

Also, the indicator substance could be a luminescent substance that would emit light as a result of microbial growth and metabolism, such as, ATP with luciferin/luciferase enzyme or a chemiluminescent material such as luminal.

Fluorescent materials may also be utilized as indicator substances in the liquid phase of the present invention. Typical fluorescent agents include umbeliferons and coumarins.

After a test sample has been placed in the liquid phase of the container, the container is incubated at an appropriate temperature, e.g., about 34° to 38° C. for about 24 to 48 hours or some other suitable time period after which changes in the indicator substances can be measured. Changes in the indicator substance are detected and measured in the semi-fluid phase by analysing the optical changes related to microorganism growth. Changes in the indicator substance can be detected and measured in the semi-fluid phase since the liquid in this phase is in equilibrium with the remaining liquid in the container. Thus, any changes which occur in the indicator substance will be present throughout the container. Detection and measurement in the semi-fluid phase free of large molecules, i.e., the sample being tested and microorganisms provides an accurate and consistent means of detecting microorganism growth with a high signal to noise ratio.

The container used in the present invention can be glass or transparent plastic such as polystyrenes. The entire container need not be transparent, but the portion of the container surrounding the semi-fluid phase must be transparent to permit measurement of any change in the indicator substance in response to microorganism growth. Also, the container can be any shape or size, but typically will be a vial or a tube which can be closed once the agar phase and liquid phase are incorporated therein. Once the two phases are loaded in the container they can be shipped to the site needed for performing analysis of test samples. No special temperature or storage requirements for the container exist.

The present invention will find particular use in the food industry to detect the presence of microorganisms or in food products. Samples of the food product can be placed in the liquid phase of the container, incubated and a reading taken in the semi-fluid phase of any change in the indicator substance. The present invention can be used to detect microorganism in clinical samples such as body fluids.

The following examples illustrate the use of the present invention with reference to the Figures.

EXAMPLE 1

Total Bacterial Count in Milk

Figure 2:
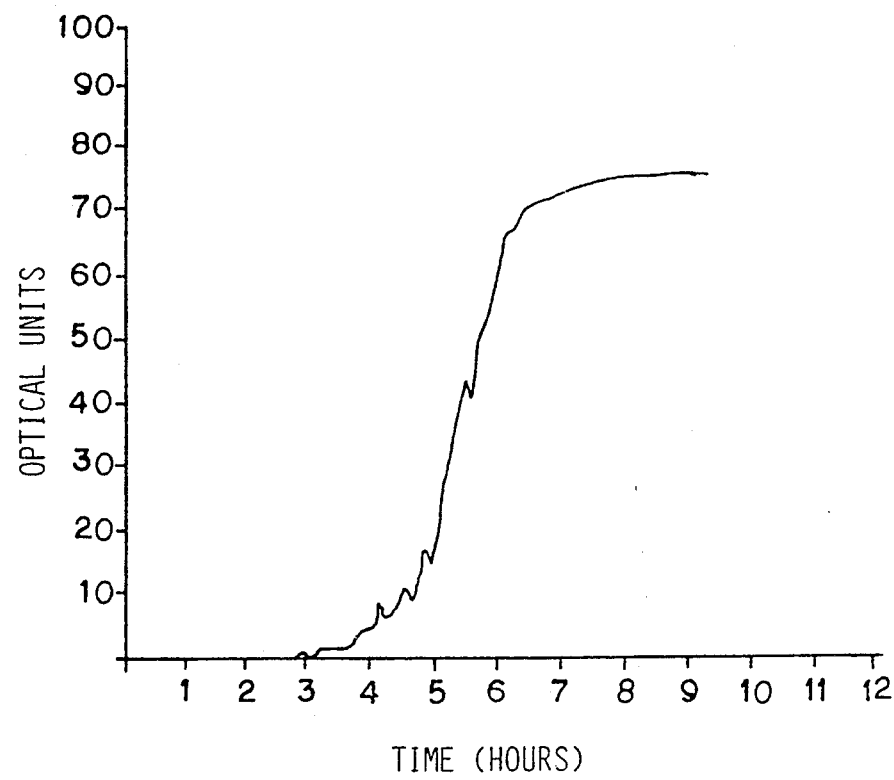
FIG. 2 shows total bacterial count in milk.

FIG. 2 illustrates the curve generated by using the following procedure:

Bottom layer includes: Plate count agar (Difco, Detroit, Mich.) with 0.032 gr/l of Bromcresol Purple (BCP). Top (liquid) layer Plate count broth (Difco) with the same concentration of BCP. Add 0.5 ml of the bottom solution to the disposable and allow to solidify. Add 2 ml of the liquid layer to the container containing the solidified medium. Add 0.1–0.5 ml of milk (test sample) and insert into the instrument. The instrument monitors the vial while incubating it at 35° C.

EXAMPLE 2

Coilforms in Water

Figure 3:
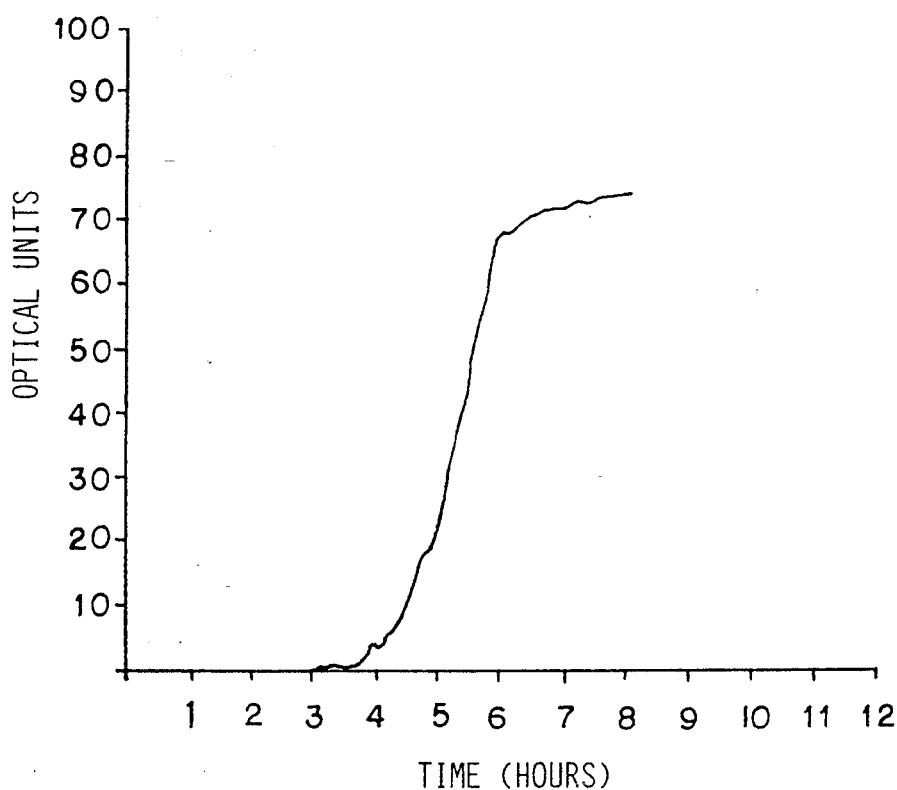
FIG. 3 shows detection of coliform in water.

FIG. 3 illustrates the curve obtained for the detection of coliforms in water. Both medium layers utilized the medium described by Firstenberg-Eden and Klein (J. Food Sci. 48:1307–1311). The bottom layer contained 1.5 g/l of agar. One-half milliliter of water was added to the top broth and the vial was monitored by the instrument at 35° C.

EXAMPLE 3

Yeast in Orange Juice

Figure 4:
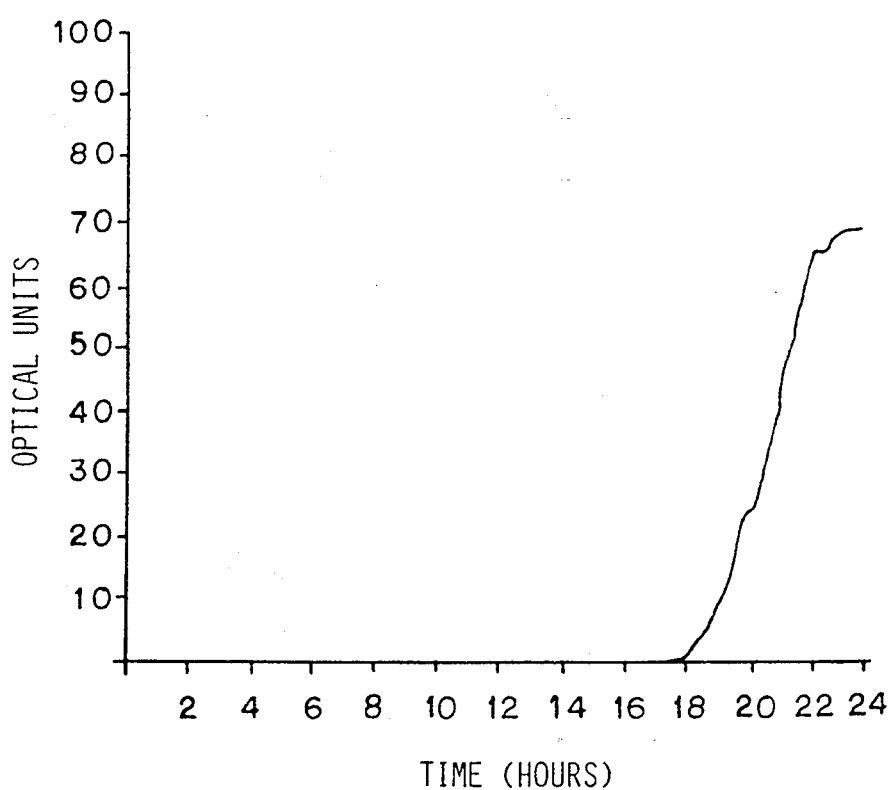
FIG. 4 shows growth of yeast in orange juice.

The growth of yeast resulted in the curve shown in FIG. 4. The medium utilized is Yeast Carbon Base Medium (Difco) with 3.0 gr/l Ammonium Sulfate and 0.030 gr/l of Bromcresol Green (BCG). 0.2 ml of contaminated orange juice was added to the top layer and the vial was monitored at 30° C.

Similar results can be obtained with the utilization of selective media for the detection of *Staphylococcus aures, E. coli*, Salmonella, Listeria, etc.

By utilizing the method described by Bishop, et al., (J. Food Prot., 1984, 47:471–475), with the addition of resazurin as the dye, the shelf life of milk and other perishable foods can be assessed.

The invention has been described in an illustrative manner, and it is to be understood that the terminology which has been used is intended to be in the nature of words of description rather than of limitation.

Obviously many modifications and variations of the present invention are possible in light of the above teachings. It is, therefore, to be understood that within the scope of the appended claims the invention may be practiced otherwise than as specifically described.

What is claimed is:

1. A device for detecting microbial growth from a sample substance, said device comprising:
   a container which is at least partially transparent and includes an inner chamber;
   a fluid layer contained within said container for cultivating microorganisms therein, said fluid layer having a volume;
   a soluble growth media and at least one indicator substance mixed with said fluid layer for undergoing transformation in the presence of microorganism growth; and
   a barrier layer having a volume smaller than said volume of said fluid layer contained within said container adjacent to said fluid layer, said barrier layer composed of a matrix phase containing a fluid which contains at least one indicator substance and soluble growth media essentially identical to that contained in said fluid layer, said barrier layer fluid being in equilibrium with said fluid layer, said barrier layer providing a barrier to solid substances introduced into said fluid layer while providing a fluid zone within said matrix which facilitates change in said indicator substance and growth media contained in said fluid in said matrix, said change occurs and can be detected in said indicator substance contained in said fluid in said matrix due to microbial growth occurring in said fluid layer.

2. The device of claim 1 wherein said container is constructed so as to be sealed.

3. The device as set forth in claim 1 wherein said barrier layer is an agar.

4. The device of claim 1 wherein the indicator substance is a dye.

5. The device of claim 4 wherein said barrier layer is an agar.

6. The device of claim 1 wherein the indicator substance is a luminescent or fluorescent material.

7. The device of claim 6 wherein said barrier layer is an agar.

8. A method for the detection of microorganisms and microorganism activity in a substance, the method comprising the steps of:
   adding the substance to a fluid layer having a volume contained within a container, the fluid layer containing soluble growth media and at least one indicator substance mixed therein, said indicator substance undergoing a transformation in the presence of microorganisms;
   equilibrating concentrations of all soluble materials present in the fluid layer with a fluid contained within a barrier layer while the barrier layer prevents solid substances from entering therein, said barrier layer having a volume smaller than said volume of said fluid layer, and being composed of a matrix phase containing at least one indicator substance and soluble growth media essentially identical to that contained in said fluid layer; and
   detecting the transformations of the indicator substance and growth media occurring in both the fluid layer and the barrier layer by detecting changes in the fluid contained in the barrier layer.

9. The method of claim 8 wherein the indicator substance is a dye.

10. The method of claim 9 wherein the barrier layer is an agar.

11. The method of claim 8 wherein the indicator substance is a luminescent or fluorescent substance.

12. The method of claim 11 wherein the barrier layer is an agar.

13. The method of claim 8 wherein the changes in the indicator substance are detected photometrically.

14. The method of claim 13 wherein the barrier layer is an agar.

* * * * *